(12) United States Patent
Finnegan

(10) Patent No.: US 10,047,381 B2
(45) Date of Patent: Aug. 14, 2018

(54) METHOD FOR PRODUCING 3-HYDROXYPROPANAL

(71) Applicant: Verdant Bioproducts Limited, Milton Keynes (GB)

(72) Inventor: Irene Finnegan, Milton Keynes (GB)

(73) Assignee: VERDANT BIOPRODUCTS LIMITED, Milton Keynes (GB)

( * ) Notice: Subject to any disclaimer, the term of this patent is extended or adjusted under 35 U.S.C. 154(b) by 0 days.

(21) Appl. No.: 15/504,496

(22) PCT Filed: Aug. 19, 2015

(86) PCT No.: PCT/GB2015/052410
§ 371 (c)(1),
(2) Date: Feb. 16, 2017

(87) PCT Pub. No.: WO2016/027088
PCT Pub. Date: Feb. 25, 2016

(65) Prior Publication Data
US 2017/0233773 A1  Aug. 17, 2017

(30) Foreign Application Priority Data
Aug. 19, 2014 (GB) .................................. 1414737.5

(51) Int. Cl.
| | | |
|---|---|---|
| C12P 7/24 | (2006.01) | |
| C12P 7/62 | (2006.01) | |
| C12N 1/20 | (2006.01) | |
| B01D 3/14 | (2006.01) | |
| B01D 61/14 | (2006.01) | |

(52) U.S. Cl.
CPC ............... *C12P 7/24* (2013.01); *B01D 3/145* (2013.01); *B01D 61/147* (2013.01); *C12N 1/20* (2013.01); *B01D 2311/2669* (2013.01); *C12P 7/62* (2013.01)

(58) Field of Classification Search
CPC .................. C12P 7/24; C12P 7/62; C12N 1/20
USPC ........................... 435/252.1, 243, 147, 254.4
See application file for complete search history.

(56) References Cited

U.S. PATENT DOCUMENTS

| | | | |
|---|---|---|---|
| 4,962,027 A | 10/1990 | Slininger et al. | |
| 6,852,517 B1 | 2/2005 | Suthers et al. | |
| 7,186,541 B2 | 3/2007 | Gokarn et al. | |
| 8,338,145 B2 | 12/2012 | Tsobanakis et al. | |
| 2016/0348017 A1 | 12/2016 | Finnegan | |
| 2016/0348137 A1 | 12/2016 | Finnegan | |

FOREIGN PATENT DOCUMENTS

| | | |
|---|---|---|
| WO | 2013011292 A2 | 1/2013 |
| WO | 2015118341 A | 8/2015 |

OTHER PUBLICATIONS

Coban et al. "Effect of various carbon and nitrogen sources on cellulose syntheseis by Acetobacter lovaniensis HBB5", African Journal of Biotechnology, vol. 10(27), Jun. 15, 2011, pp. 5346-5354.
Krauter, Hendrik, et al., Production of high amounts of 3-hydroxypropionaldehyde from glycerol bywith strongly increased biocatalyst lifetime and productivity, New Biotechnology, vol. 29, No. 2, Jan. 2012, pp. 211-217.
Sardari, Roya et al., "Biotransformation of glycerol to 3 hydroxpropionaldehyde: Improved production by in situcomplexation with bisulfite in a fed-batch mode and separation on anion exchanger", Journal of Biotechnology, vol. 168, No. 4, Sep. 21, 2013, pp. 534-542.
Tarek, Dishisha et al., "Flux analysis of the *Lactobacillus reuteri* propanediol-utilization pathway for production of 3-hyroxypropionaldehyde, 3-hydroxypropionic acid and 1, 3-propanediol from glycerol", Microbial Cell Factories, Biomed Central, London, NL, vol. 13, No. 1, May 27, 2014, 76 (11 pages).
Vollenwider, Sabine et al., "Purification and structural characterization of 3-hydroxypropionaldehyde and its derivatives." Journal of Agricultural and Food Chemistry, vol. 51, No. 11, May 21, 2003, pp. 3287-3293.

*Primary Examiner* — Tekchand Saidha
*Assistant Examiner* — Mohammad Y Meah
(74) *Attorney, Agent, or Firm* — Cantor Colburn LLP

(57) ABSTRACT

There is described a method for producing 3-hydroxypropanal, the method comprising: culturing an *Acetobacter lovaniensis* bacterium in a growth medium containing phosphate at a level which is more than 1 g/liter and nitrate at a level which is more than 0.1 g/liter, wherein culturing of the bacterium produces the 3-hydroxypropanal. The 3-hydroxypropanal can be separated from the growth medium or, when the microorganism has converted some or all of the 3-hydroxypropanal to 3-hydroxypropionic acid and/or a 3-hydroxypropionate ester, it may be separated as 3-hydroxypropionic acid or a 3-hydroxypropionate ester. The separated product can be converted into other chemicals such as an ester of 3-hydroxypropionic acid, 3-hydroxypropionic acid, 3-hydroxypropionate salts (including ammonium, sodium and calcium 3-hydroxypropionate), acrylic acid, acrylates, acrylamide, acrylonitrile, acrolein and 1,3 propanediol.

17 Claims, 3 Drawing Sheets

METHOD FOR PRODUCING 3-HYDROXYPROPANAL

CROSS REFERENCE TO RELATED APPLICATIONS

This application is a U.S. National Stage application of PCT/GB2015/052410, filed Aug. 19, 2015, which claims priority to GB Application No. 1414737.5, filed Aug. 19, 2014, both of which are incorporated by reference in their entirety herein.

FIELD OF THE INVENTION

The present invention relates to a method for producing 3-hydroxypropanal (3HPA) by culturing an *Acetobacter* microorganism under particular growth conditions. 3-hydroxypropanal is a potent broad spectrum anti-microbial agent normally produced by bacteria when fermenting glycerol. 3-hydroxypropanal can be produced readily in commercial quantities in the present invention. If desired, 3-hydroxypropanal can be converted to a range of other commercially useful products.

BACKGROUND TO THE INVENTION 3-hydroxypropanal (3HPA) (also called Reuterin and 3-hydroxypropionaldehyde) is a broad spectrum anti-microbial agent produced by a number of microorganisms when fermenting glycerol under anaerobic conditions. Most noted of these are *Lactobacillus reuteri* (Talarico T. L. et al., *Anti Microbial Agents and Chemotherapy* (1988), 32, 1854-1858). However, *Citrobacter freundii* (Daniel, R. et al., *J Bacteriol.* (1995), 2151-2156), *Clostridium butyricum* (Malaoui, H. and Marczak, R., *Enzyme and Microbial Technology* (2000), 27, 399-405), *Enterobacter agglomerans* (Barbirato, F. et al., *Applied and Environ. Microbiol.* (1996), 62, 4405-4409) and *Klebsiella pneumonia* (Sliminiger, P. J. et al., *Appl. Environ. Microbiol.* (1983), 50, 1444-1450) have all been shown to synthesise 3HPA under similar conditions.

The production of 3HPA is limited by its anti-microbial effect. As levels accumulate in the fermentation broth, it becomes toxic. A maximal level of synthesis of 170 mM of 3HPA has been noted for *Lactobacillus reuteri* when growing on 200 mM glycerol (Vollenweider, S. et al., *J. Agric. Food Chem.* (2003), 51, 3287-3293). This currently limits the use of this potentially useful anti-microbial agent to probiotics. Synthesis of this compound at higher levels would be of great commercial advantage.

3HPA is a co-product synthesised by relevant bacteria when metabolising glycerol to 1,3 propandiol via glycerol diol dehydrase, a B12 dependant enzyme (Vollenweider, S. et al., *J. Agric. Food Chem.* (2003), 51, 3287-3289). 3HPA is normal present as a complex mixture consisting of the 3HPA, its hydrate and its dimer. At higher concentrations (greater than 10%) 3HPA exists predominantly as the dimer. In vivo, the hydrate form is predominant. 3HPA also polymerises to form condensation products and the type of polymer depends on whether growth conditions are acidic or basic.

The anti-microbial effect is thought to be due to activity against sulphydryl containing enzymes, in particular the B1 subunit of ribonucleotide reductase (which accounts for its broad anti-microbial effect) and thioredoxin (Schaefer, L. et al., *Microbiology* (2010), 156, 1589-1599). 3HPA was found to be active against coliforms at levels of 50-100 U/g (where a unit is equivalent to 5 u/ml) (Daeschel. M. A., *Food Technol.* (1989), 43, 164-167), against *E. coli, P. aeruginosa, S. aureus* and *B. subtilis* at levels of 20-35 ppm (Chen, C. N. et al., *J. Biomed. Res.* (2002), 61, 360-369) and against protozoa at between 35 and 70 uM (Yunmbam, M. K. and Roberts. J. F., *Comp. Biochem. Physiol. C.* (1992), 101, 235-238). Producing strains can tolerate up to 30 mM (Barbirato F. et al., *Applied Environ. Microbiol.* (1996), 62, 1448-1451) and the LD50 in vertebrates (mice) has been recorded as 1,500 U or 7.5 mg (Yunmbam, M. K. and Roberts, J. F. *Comp. Biochem. Physiol. C* (1993), 105, 521-524).

3HPA is generally produced in a two-step process. In the first step, the bacterium is cultured overnight at 37° C. in MRS broth. The cell mass is then recovered by centrifugation and washed in phosphate buffer. In a second step, the cells are suspended to a dry cell weight of 10 mg/ml in 250 mMol/l glycerol and incubated anaerobically at 37° C. Up to 85% of the glycerol is converted to 3HPA. This is a yield of approximately 19 g/l or 1.9%. The key step in this process is the dehydration of glycerol by B12 dependant glycerol dehydratase. The ability to produce 3HPA more readily at higher concentrations, not only as an antibiotic agent but also as a platform molecule for other useful commercial molecules such as 3-hydroxypropionic acid (3HP), which can be converted to esters of 3HP, esters of acrylic acid, acrylic acid (AA), acryamide and acrylic polymers, 1,3 propanediol, and acrolein (Vollenweider, S. and Lacroix, C., *Applied Microbiol.* (2004), 64, 16-27), would be commercially advantageous. However, 3HPA is generally a complex mixture of molecules whose composition depends on culture conditions such as pH. There have been attempts to commercialize this process via optimisation of glycerol fermentation (Slininger, P. J. and Bothast, R. J., *Applied Environ. Microbiol.* (1985), 50, 1444-1450) and the trapping of the 3HPA as the semicarbazide to overcome the toxic effects of the compound (Ulmer, C., et al., *Chem. Ing. Tech.* (2002), 74, 674). Levels of 621 mM of 3HPA have been reported (which is equivalent to 44.71 g per liter) for this method (Talarico, T. L., et al., *Antimicrobio. Agents Chemother.* (1989), 33, 674-679). However, commercial production through a bacterial system has not yet been successful.

WO2013/011292 describes a microorganism which is capable of producing long chain aliphatic carboxylic acids. This document describes a particular strain referred to as *Acetobacter lovaniensis* FJ1 having accession number NCIMB 41808 (deposited at NCIMB Ltd. (Ferguson Building, Craibstone Estate, Bucksburn, Aberdeen, AB21 9YA) on 12 Jan. 2011 under the provisions of the Budapest Treaty).

SUMMARY OF THE INVENTION

It has been surprisingly found that the *Acetobacter lovaniensis* strain described in WO2013/011292 can produce 3HPA. It was not previously known that this microorganism could produce this product. Further, this microorganism can produce 3HPA at commercially viable yields.

The present invention relates to a method for producing 3HPA using the microorganism described in WO2013/011292. The disclosure of WO2013/011292 is incorporated herein in its entirety. This microorganism has been shown to have the ability to produce 3HPA when grown using a medium containing phosphate and nitrate.

In a first aspect, the present invention provides a method for producing 3HPA, the method comprising: culturing an *Acetobacter lovaniensis* bacterium in a growth medium containing phosphate at a level which is more than 1 g/liter and nitrate at more than 0.1 g/liter, wherein culturing of the bacterium produces 3HPA.

The term "3-hydroxypropanal" or "3HPA" covers 3HPA in all of its various forms. For example, it covers 3HPA as a hydrate, a monomer, a dimer, a trimer, a tetramer, a polymer and any other form in which it may be produced. 3-hydroxypropanal is biologically active in many forms so long as it retains an aldehyde functionality. Activity is lost at high pH because of the tendency to react through the aldehyde group.

The *Acetobacter lovaniensis* bacterium in cultured in a growth medium containing more than 1 g/liter of phosphate. 1 g/liter is the amount of phosphate ion ($PO_4^{3-}$) in the growth medium rather than the amount of the phosphate containing compound in the growth medium. For example, potassium dihydrogen phosphate ($KH_2PO_4$) has a relative molecular mass of 136. The phosphate part of this has a relative molecular mass of 95. Therefore, if 136 grams of $KH_2PO_4$ was added to 100 liters of water, there would be 1.36 g/liter of $KH_2PO_4$ in the water but there would be 0.95 g/liter of phosphate in the water.

In some embodiments, the growth medium preferably contains phosphate at a level which is more than 2 g/liter. In other embodiments, the growth medium contains phosphate at more than 3 g/liter. In further embodiments, the growth medium contains phosphate at more than 4 g/liter. In particular embodiments, the growth medium contains phosphate at more than 5 g/liter. In some embodiments, the growth medium contains phosphate at more than 6 g/liter. In other embodiments, the growth medium contains phosphate at more than 7 g/liter. In further embodiments, the growth medium contains phosphate at more than 8 g/liter. In particular embodiments, the growth medium contains phosphate at more than 9 g/liter. In some embodiments, the growth medium contains phosphate at more than 10 g/liter. In other embodiments, the growth medium contains phosphate at more than 11 g/liter. In further embodiments, the growth medium contains phosphate at more than 12 g/liter. In a preferred embodiment, the growth medium contains phosphate at more than 13 g/liter. In another preferred embodiment, the growth medium contains phosphate at more than 14 g/liter.

In some embodiments, the growth medium contains phosphate at a level which is less than 150 g/liter. In other embodiments, the growth medium contains phosphate at less than 100 g/liter. In further embodiments, the growth medium contains phosphate at less than 80 g/liter. In various embodiments, the growth medium contains phosphate at less than 70 g/liter. In particular embodiments, the growth medium contains phosphate at less than 60 g/liter. In some embodiments, the growth medium contains phosphate at less than 50 g/liter. In other embodiments, the growth medium contains phosphate at less than 45 g/liter. In further embodiments, the growth medium contains phosphate at less than 40 g/liter. In particular embodiments, the growth medium contains phosphate at less than 35 g/liter. In some embodiments, the growth medium contains phosphate at less than 30 g/liter. In other embodiments, the growth medium contains phosphate at less than 25 g/liter. In further embodiments, the growth medium contains phosphate at less than 20 g/liter. In particular embodiments, the growth medium contains phosphate at less than 15 g/liter.

In some embodiments, the growth medium contains phosphate at a level which is between 1 and 150 g/liter. In other embodiments, the growth medium contains phosphate at between 2 and 100 g/liter. In further embodiments, the growth medium contains phosphate at between 3 and 80 g/liter. In various embodiments, the growth medium contains phosphate at between 4 and 70 g/liter. In particular embodiments, the growth medium contains phosphate at between 5 and 60 g/liter. In some embodiments, the growth medium contains phosphate at between 6 and 50 g/liter. In other embodiments, the growth medium contains phosphate at between 7 and 45 g/liter. In further embodiments, the growth medium contains phosphate at between 8 and 40 g/liter. In particular embodiments, the growth medium contains phosphate at between 9 and 35 g/liter. In some embodiments, the growth medium contains phosphate at between 10 and 30 g/liter. In other embodiments, the growth medium contains phosphate at between 11 and 25 g/liter. In further embodiments, the growth medium contains phosphate at between 12 and 20 g/liter. In particular embodiments, the growth medium contains phosphate at between 13 and 15 g/liter.

The *Acetobacter lovaniensis* bacterium in cultured in a growth medium containing more than 0.1 g/liter of nitrate. 0.1 g/liter is the amount of nitrate ion ($NO_3^-$) in the growth medium rather than the amount of the nitrate containing compound in the growth medium. For example potassium nitrate ($KNO_3$) has a relative molecular mass of 101. The nitrate part of this has a relative mass of 62. Therefore if 101 grams of potassium nitrate was added to 100 liters of water, there would be 1.01 g/liter of potassium nitrate in the water but 0.62 g/liter of nitrate in the water.

In some embodiments, the growth medium preferably contains nitrate at a level which is more than 0.2 g/liter. In other embodiments, the growth medium contains nitrate at more than 0.3 g/liter. In further embodiments, the growth medium contains nitrate at more than 0.4 g/liter. In particular embodiments, the growth medium contains nitrate at more than 0.5 g/liter. In some embodiments, the growth medium contains nitrate at more than 0.6 g/liter. In other embodiments, the growth medium contains nitrate at more than 0.7 g/liter. In further embodiments, the growth medium contains nitrate at more than 0.8 g/liter. In particular embodiments, the growth medium contains nitrate at more than 0.9 g/liter. In other embodiments, the growth medium contains nitrate at more than 1 g/liter. In a preferred embodiment, the growth medium contains nitrate at more than 1.1 g/liter. In another preferred embodiment, the growth medium contains nitrate at more than 1.2 g/liter.

In some embodiments, the growth medium contains nitrate at a level which is less than 10 g/liter. In other embodiments, the growth medium contains nitrate at less than 5 g/liter. In further embodiments, the growth medium contains nitrate at less than 3 g/liter. In various embodiments, the growth medium contains nitrate at less than 2.5 g/liter. In particular embodiments, the growth medium contains nitrate at less than 2 g/liter. In some embodiments, the growth medium contains nitrate at less than 1.8 g/liter. In other embodiments, the growth medium contains nitrate at less than 1.7 g/liter. In further embodiments, the growth medium contains nitrate at less than 1.6 g/liter. In particular embodiments, the growth medium contains nitrate at less than 1.5 g/liter. In some embodiments, the growth medium contains nitrate at less than 1.4 g/liter. In other embodiments, the growth medium contains nitrate at less than 1.3 g/liter.

In some embodiments, the growth medium contains nitrate at a level which is between 0.1 and 10 g/liter. In other embodiments, the growth medium contains nitrate at between 0.2 and 5 g/liter. In further embodiments, the growth medium contains nitrate at between 0.3 and 3 g/liter. In various embodiments, the growth medium contains nitrate at between 0.4 and 2.5 g/liter. In particular embodiments, the growth medium contains nitrate at between 0.5 and 2 g/liter. In some embodiments, the growth medium contains nitrate at between 0.6 and 1.8 g/liter. In other embodiments, the growth medium contains nitrate at between 0.7 and 1.7 g/liter. In further embodiments, the growth medium contains nitrate at between 0.8 and 1.6 g/liter. In particular embodiments, the growth medium contains nitrate at between 0.9 and 1.5 g/liter. In some embodiments, the growth medium contains nitrate at between 1 and 1.4 g/liter. In other embodiments, the growth medium contains nitrate at between 1.1 and 1.3 g/liter.

The growth medium can be any suitable growth medium which allows the *Acetobacter lovaniensis* bacterium to grow and reproduce, and to produce 3HPA. The growth medium may contain various ingredients/nutrients to allow the bacterium to grow and reproduce. The growth medium may contain one or more of the following additives: a potassium salt, a magnesium salt, a manganese salt, an iron salt, a copper salt, a cobalt salt, a sodium salt, a zinc salt, a calcium salt, a molybdenum salt, a chloride, a sulphate, a molybdate and a carbonate. These additives are generally present in the growth medium at between 0.01 and 2 g/liter.

In some embodiments, the growth medium may have one or more of the following additives in the amount specified:

| Ingredient | g/litre |
|---|---|
| Potassium hydrogen phosphate | 10-30 |
| Potassium nitrate | 1-3 |
| Magnesium chloride | 0.1-20 |
| Manganese chloride | 0.01-0.1 |
| Ferric chloride | 0.01-0.1 |
| Copper sulphate | 0.01-0.1 |
| Cobalt chloride | 0.01-0.1 |
| Sodium molybdate | 0.01-0.1 |
| Zinc chloride | 0.1-1 |

In a particular embodiment, the growth medium has the following composition:

| Ingredient | g/litre |
|---|---|
| Potassium hydrogen phosphate | 20 |
| Potassium nitrate | 2 |
| Magnesium chloride | 1 |
| Manganese chloride | 0.05 |
| Ferric chloride | 0.05 |
| Copper sulphate | 0.05 |
| Cobalt chloride | 0.05 |
| Sodium molybdate | 0.05 |
| Zinc chloride | 0.5 |

The bacterium can fix carbon dioxide. Therefore, the growth medium does not require an exogenous source of carbon other than carbon dioxide dissolved in the growth medium from the atmosphere. However, in some embodiments, before the bacterium is cultured or during culturing, carbon dioxide can be bubbled through the growth medium to increase the amount of carbon dioxide dissolved in the growth medium. The bacterium can use carbon dioxide as the sole source of carbon. In some embodiments, no carbon source is present other than carbon dioxide. For example, in preferred embodiments, the growth medium does not contain glycerol.

The growth medium may have a pH of between 3.5 and 8.5. Preferably, the growth medium has a pH of between 4 and 7. More preferably, the growth medium has a pH of about 4.5. The pH of the growth medium may be adjusted to control the form in which the 3HPA is present.

The growth medium is preferably aqueous such that the nutrients/additives are dissolved in water.

The bacterium is generally cultured at a temperature of between 0° C. and 60° C. Preferably, the bacterium is cultured at a temperature of between 10° C. and 40° C. In some embodiments, the bacterium is cultured at a temperature of between 15° C. and 30° C.

The bacterium is generally cultured until the growth culture reaches an optical density when measured at 600 nm ($OD_{600}$) of between 0.75 and 1.0.

During culturing, the culture can be diluted with additional growth medium to increase the volume of culture. Therefore, when it is desired to extract the 3HPA, the culture should have a final optical density of between 0.75 and 1.0.

The bacterium may be cultured for between 12 and 36 hours. In some embodiments, the bacterium may be cultured for between 18 hours and 30 hours.

The 3HPA is produced by culturing an *Acetobacter lovaniensis* bacterium. The bacterium can be any suitable *Acetobacter lovaniensis* bacterium which can produce 3HPA. This includes strain FJ1 (having the accession number NCIMB 41808) and similar strains which are related to or derived from FJ1. The term "derived from" means that FJ1 can be modified or mutated to produce further bacteria. For example, genes may be inserted or removed from FJ1. Bacteria which are derived from FJ1 should be functionally equivalent to FJ1 and should be able to produce 3HPA. Further, the derived bacterium should be able to grow under the same conditions as FJ1. Preferably, the bacterium is strain FJ1 having accession number NCIMB 41808. A bacterium can be identified as an *Acetobacter lovaniensis* bacterium by methods which are well known to those skilled in the art, for example, by using 16S rDNA analysis.

The bacterium produces 3HPA as it grows so once the culturing of the bacterium has been completed, the 3HPA will be present in the growth medium. The 3HPA can then be extracted, if desired.

The method may further comprise the step of separating the 3HPA from the growth medium. This can be in a first separation step. This can be done in any suitable way and a number of methods will be apparent to one skilled in the art.

For example, the 3HPA can be separated using distillation, including standard distillation, fractional distillation, vacuum distillation, distillation with an entrainer, solvent extraction followed by recovery with distillation, and continuous distillation or thin film extraction. Other separation methods include membrane perfusion, electro-chemical separation, or the use of supercritical carbon dioxide.

If distillation is carried out at 1 atmosphere (rather than at reduced pressure as in vacuum distillation) using, for example, a side arm condenser, the 3HPA will be concentrated as the water content is reduced and contaminating fractions removed.

The microorganism produces 3HPA when it is being cultured. However, this 3HPA may then be converted into other compounds by the microorganism. For example, the 3HPA may be esterified to produce an ester of 3HPA. Alternatively, the 3HPA may be converted into 3HP (3-hydroxypropionic acid). In some embodiments, the 3HPA may be converted to an ester of 3HPA which in turn is converted to 3HP. Therefore, the method may involve separating 3HPA, 3HP and/or 3HP ester from the growth medium in embodiments in which the microorganism has converted some or all of the 3HPA to 3HP and/or 3HP ester.

The ester form of 3HPA may be referred to herein as "3HPA ester", "ester of 3HPA", "3HP ester" or "ester of 3HP". All these terms are equivalent are refer to the same compounds. This is an alkyl 3-hydroxypropionate. If the 3HPA ester is the ethyl ester of 3HPA (or "3HPA ethyl ester", "3HP ethyl ester" or "ethyl ester of 3HP"), this refers to ethyl 3-hydroxypropionate.

The 3HPA can be recovered from the growth medium as 3HPA, 3HP or 3HP ester. An initial separation step can be followed by a secondary step to purify the products. This second separation can be carried out using any suitable method. For example, the 3HPA can be separated using distillation, including standard distillation, fractional distillation, vacuum distillation, distillation with an entrainer, solvent extraction followed by recovery by distillation, and continuous distillation, or thin film extraction. Other separation methods include membrane perfusion or the use of supercritical carbon dioxide.

If distillation is carried out at 1 atmosphere (rather than at reduced pressure as in vacuum distillation) using, for example, a fractionating column, the 3HPA will concentrate as the water content is reduced and contaminating fractions removed.

After the second separation step, a relatively pure sample of 3HPA is produced, generally as an aqueous solution. The residual salts and debris may be removed with a combination of flocculating and chelating agents. These include but are not limited to alum, zinc salts, calcium salts, and pectin.

Once separated, the water content of the 3HPA may be reduced. This can be done with drying agents such as, but not limited to, chloride salts (calcium or sodium) or molecular sieve 3A. Alternatively, the water content can be further reduced by distillation.

Once the 3HPA has been separated, it can be converted to a number of other chemically useful products. Suitable methods are well known to a skilled person. For example, 3HPA can be converted to the acid by oxidation either chemically or enzymatically. 3-hydroxypropionic acid (3HP) is recognised as a platform molecule which can be converted to acrylic acid. The 3HPA can be converted to the ester form either by the addition of an alcohol to the distillation process as an entrainer, or by standard chemical reaction in the presence of suitable alcohol and a catalyst. The alcohol can be any alcohol between C1 and C6. Alternatively, the generation of ethanol from acetate by *Acetobacter lovaniensis* FJ1 can be exploited to the same effect in vivo.

As indicated above, 3HPA is a platform chemical so it can then be further processed into other chemicals such as 3HP, 3-hydroxypropionate salts (including ammonium, sodium and calcium 3-hydroxypropionate), acrylic acid, acrylates, acrylamide, acrylonitrile, acrolein and 1,3 propanediol.

In a particular embodiment, there is provided a method for producing 3HPA, the method comprising:
  culturing *Acetobacter lovaniensis* strain FJ1 having accession number NCIMB 41808 in a growth medium containing phosphate at a level which is between 10 and 30 g/liter and nitrate at a level which is between 0.6 and 1.8 g/liter, wherein culturing of the bacterium produces 3HPA; and
  separating the 3HPA from the growth medium.

In this embodiment, the phosphate level is described as being between 10 and 30 g/liter and the nitrate level is described as being between 0.6 and 1.2 g/liter. However, any of the levels described above can be used in this particular embodiment in any combination. For example, the phosphate level may be more than 1 g/liter or the phosphate level may be between 13 and 15 g/liter, or any of the embodiments in between. Additionally, the nitrate level may be more than 0.1 g/liter or the nitrate level may be between 1.1 and 1.3 g/liter, or any of the embodiments in between.

DETAILED DESCRIPTION OF THE INVENTION

The invention will now be described in detail by way of example only with reference to the figures in which.

OVERVIEW

Figure 1:
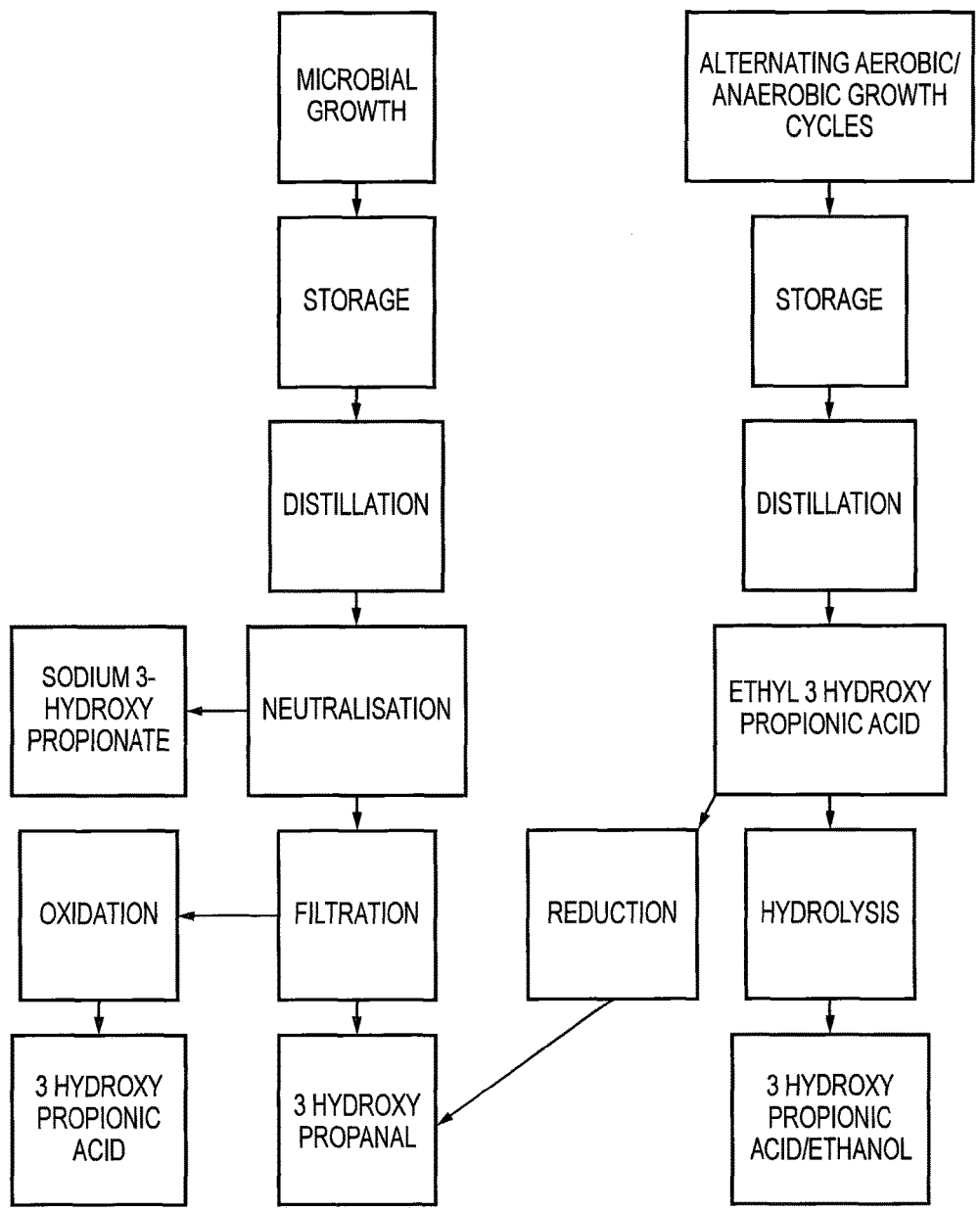
FIG. 1 is a flow diagram showing the synthesis of 3HPA and related compounds by *Acetobacter lovaniensis* FJ1 (growing on carbon dioxide in the presence of elevated levels of phosphate and nitrate) and its subsequent recovery.

In the presence of enriched levels of phosphate and exogenous nitrogen, *Acetobacter lovaniensis* FJ1 produces a different set of metabolites including, but not limited to, 3HPA. 3HPA is produced at a commercially useful level and is thought to be synthesised by the conversion of 3-hydroxypropionic acid via general reductive effect induced by the addition of nitrate.

Without wishing to be held to a particular theory, it is thought that there is a metabolic switch to carbon dioxide fixation via the hydroxyl propionate cycle (Tabita, F. J., PNAS (2009), 106, 21015-21016; Strauss, G. and Fuchs. G., Eur. J. Biochem (1993), 215, 633-643) in the presence of elevated levels of phosphate. In addition, nitrogen fixation via a nitrogenase enzyme type complex results in the generation of hydrogen (Tamagnini P., Axelssen R., Lindberg P., Oxelfelt F., Wenschiers R. and Lindblad P., Microbiology and Molecular Biology Reviews (2002), 66, 11-20) which is utilised by hydrogenase enzymes and balances the redox system of the organism. While carbon and nitrogen assimilation has been noted in other organisms (Levican G., Ugalde J. A., Ehrenfeld M., Maass A., and Parada P., BMC Genomics (2008), 581, 1186; Dubbs J. M. and Tabita F. R., FEMS Microbiol Rev. (2004), 28, 353-356; McKinlay J. B. and Harwood C. S., PNAS (2010), 1073, 1-7), the use of carbon dioxide fixation as a redox recycling mechanism via a nitrogenase system has only been previously noted in anoxygenic phototropic bacteria such as non-sulphur purple bacteria where the carbon dioxide is reduced via the Calvin Benson Basham cycle. *Acetobacter* species may be able to take advantage of this effect. While not having a functioning Calvin Benson Basham cycle, they do retain genetic elements of it, or the 3HP cycle is used to the same effect. Further to this, a proton motive force dependant efflux system for 3HP may operate as seen in *Acetobacter aceti* (Matsushiya K., Inoue T., Adachi O., and Toyama H. J., Bacteriol. (2005), 187, 4346-4352). The final production of 3HPA is thought to occur through the general reductive effect of a nitrogenase driven system.

Process For Producing 3-hydroxypropanal (3HPA) (CAS No 2134-29-4)

*Acetobacter lovaniensis* FJ1 (accession number: NCIMB 41808) is grown on a minimal salt media in which the level of phosphate and nitrate is elevated. The composition of this media is shown in the table below.

TABLE 1

Composition of Minimal Salt Media Used to Grow
*Acetobacter Lovaniensis* FJ1

| Ingredient | g/litre |
|---|---|
| Potassium hydrogen phosphate | 20.00 |
| Potassium nitrate | 2.0 |
| Magnesium chloride | 1.00 |
| Manganese chloride | 0.05 |
| Ferric chloride | 0.05 |
| Copper sulphate | 0.05 |
| Cobalt chloride | 0.05 |
| Sodium molybdate | 0.05 |
| Zinc chloride | 0.50 |

The media is dissolved in water and filtered. The water used can be either distilled water or tap water. The microorganism can be grown under non-sterile conditions and further sterilisation of media and equipment either by autoclaving or some other suitable method is not required.

The microorganism is inoculated into two liter quantities of media in shake flasks or other suitable containers and grown to an A600 of between 0.75 and 1.00. Two liters of culture media is then diluted in fresh media to a volume of 10 liters and again cultured to an A600 of between 0.75 and 1.0. The volume of the culture media is increased to the desired volume by repeated splitting of the culture.

The spent bacterial media can be stored for extended periods of time of up to twelve months.

The spent bacterial media is distilled to recover products of interest using the general process shown in FIG. 1. The spent bacterial media can be clarified before distillation either by filtration, centrifugation between 250 to 10,000 g, or through the use of flocculating agents such as alkaline salts or alum.

A standard distillation set can be used employing a flask, heater mantle, with or without fractionation column and distillation head with condenser. A vacuum can be applied provided the condenser is maintained at a temperature of less than 10° C. However, other methods of distillation such as vacuum distillation, distillation with an entrainer, solvent extraction followed by recovery with distillation, thin film extraction and continuous distillation are also applicable. Other procedures for the recovery of metabolites such as membrane perfusion, electro-chemical separation, or recovery through the use of supercritical carbon dioxide can also be employed.

Recoveries are measured after various pre-purification methods such as thin layer chromatography and solid phase adsorbents in tube formats. Solid phase adsorbent tubes are typically Cleanert C18 adsorbents in varying sizes of tube. The material is adsorbed onto the C18 and washed clean of contaminants and then eluted with either acetone or ethanol containing 0.1% HCl.

The presence of 3HPA is indicated by a positive Schiff's reaction, where the molecule behaves as a hemi acetal. The presence of the aldehyde product can further be analysed by various colorimetric assays such as that of Circle (Circle S. J. et al. (1945) *Ind. Eng. Chem. Anal,* 17, 259-262) or Doleyres (Doleyres Y et al. (2005) *Applied Microbiol,* 68, 467-474).

Figure 2:
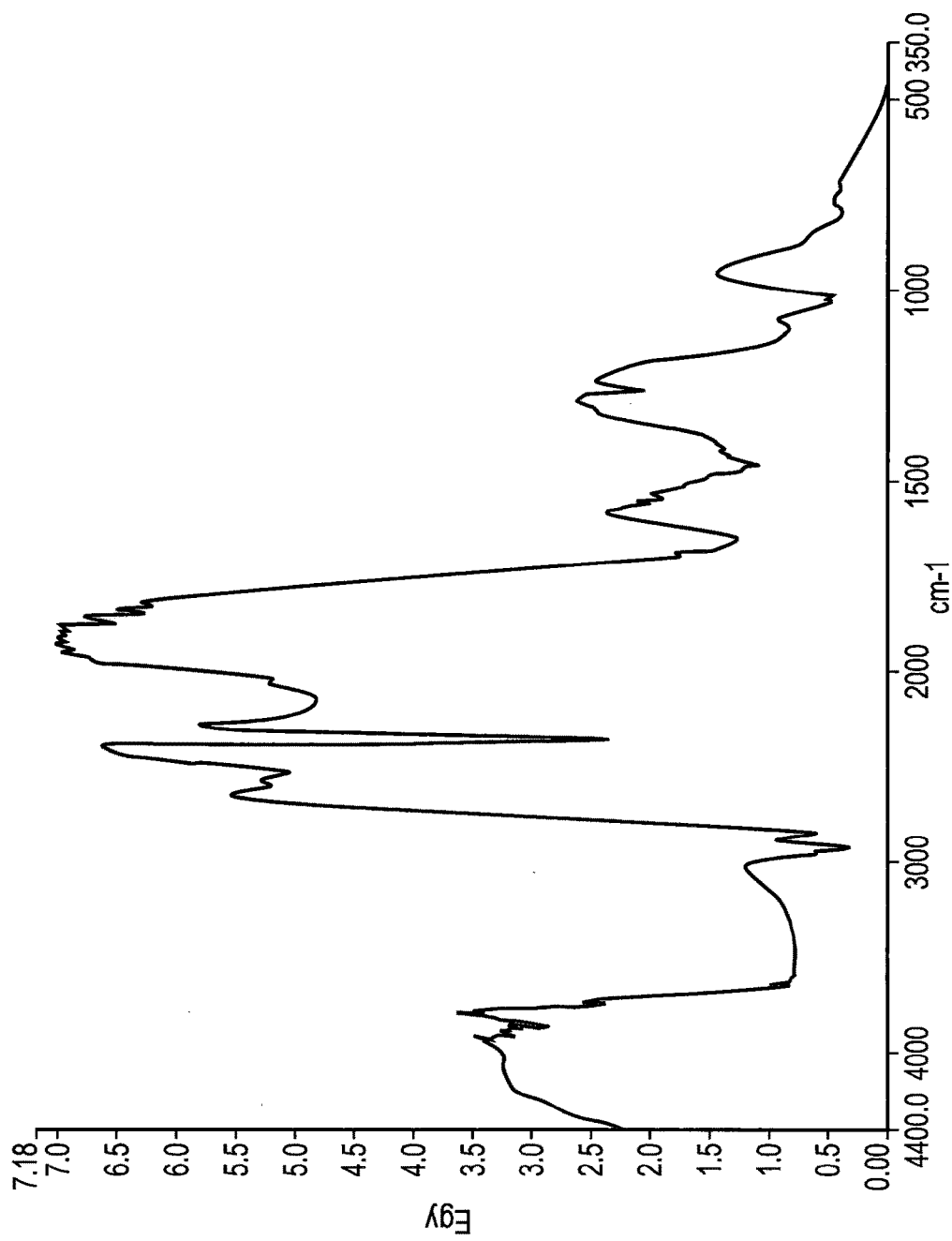
FIG. 2 is a typical infra-red scan of 3-hydroxypropanal.

Infra-red scans of purified samples are consistent with that of 3HPA with a large C—O stretch at 1050-1150 $cm^{-1}$, a broad OH stretch at 3450 $cm^{-1}$, a C═O stretch at 1730 $cm^{-1}$ and typical alkane stretches at 2880 $cm^{-1}$ and 1380 $cm^{-1}$ (FIG. 2).

The concentration of 3HPA, 3HP and 3HP ester can be measured by high pressure liquid chromatography (HPLC). Typically 3HPA, 3HP and 3HP ester is eluted isocratically using a 25 mm ODS-H, 4.6 mm column with a mobile phase consisting of 95% ethanol and 5% water.

Individual products can be identified using mass spectroscopy with and without derivatization depending on the source and the type of the sample. For samples where derivatization is required, material is extracted into a suitable solvent and then treated with BSTFA (N,O-bis(trimethylsilyl)trifluoroacetamide) or TMS (trimethyl silyl). The instrument is typically run with an injection temperature of 80° C. followed by a 7° C. per minute rise to reach a full temperature of 300° C. The column is then held for 5 minutes at this temperature. A basic library search was used to identify the peaks.

Figure 3:
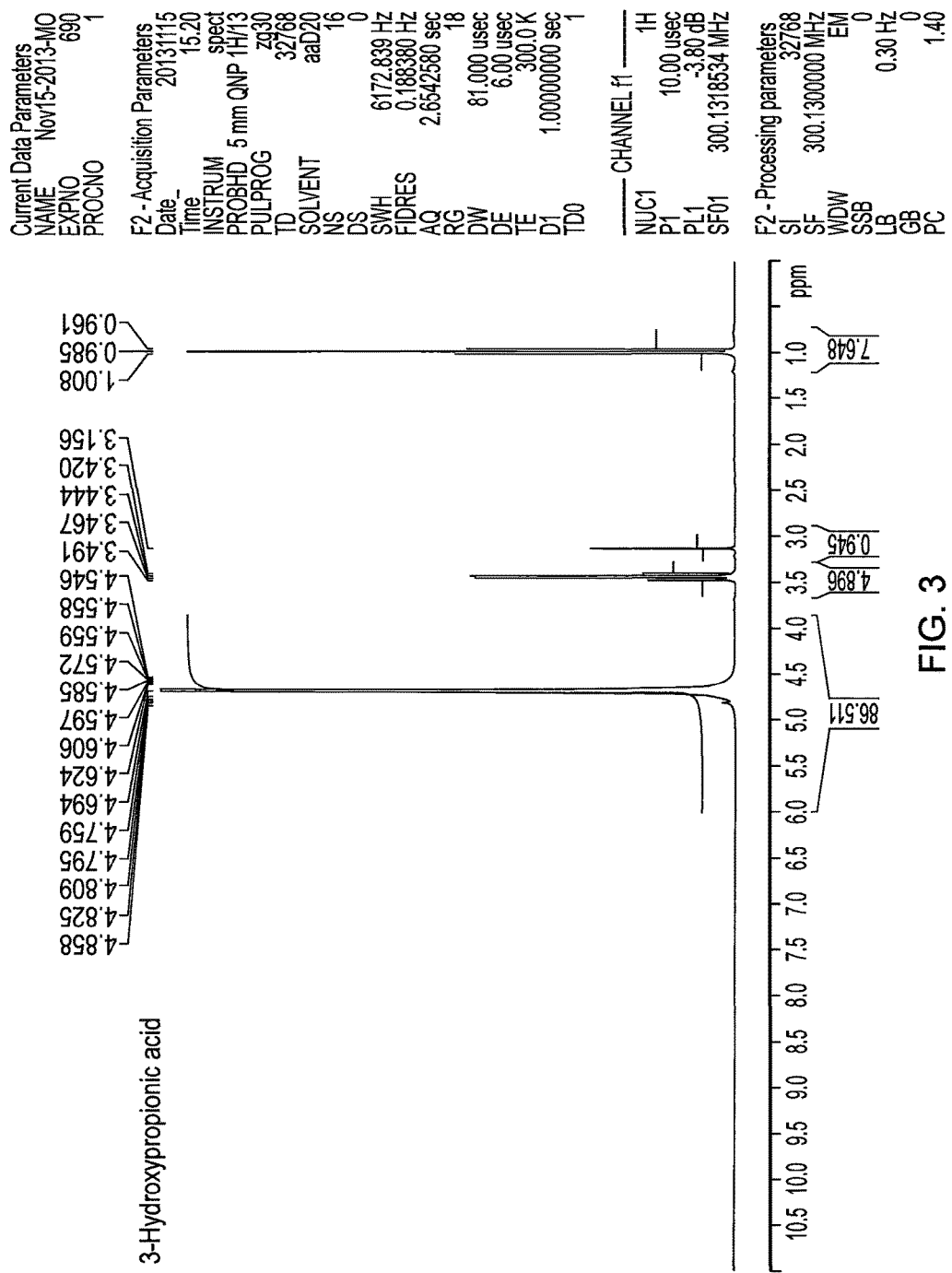
FIG. 3 is a typical NMR Scan of 3-hydroxypropionic acid derived by oxidation of the 3-hydroxypropanal hydrate.

Proton NMR scans reveal spectra typical of 3HPA in the hydrate form was not typical of an aldehyde. However, when oxidised in the presence of hydrogen peroxide, 3HPA hydrate converts to 3-hydroxypropionic acid and yields a proton NMR scan typical of 3HP (FIG. 3).

EXAMPLES

Example 1

The Growth of Organism on Carbon Dioxide as Sole Source of Carbon

The organism when grown in the presence of elevated levels of phosphate and nitrate achieves yields of 0.07 g/l/h dry cell weight at 20° C. Under these conditions the organism achieves the production of 0.267 g 3HPA/l/h/g dry cell weight of organism. This equates to a level of synthesis of 6.41% or 64.152 g/l/g/dry weight in a 24 hour period.

Example 2

The Growth of Organism on Carbon Dioxide and Alternating Between Cycles of Aerobic and Anaerobic Growth—Synthesis of 3HPA as the Ester By taking the culture through alternate cycles of aerobic growth where 3HPA and acetate form and then anaerobic growth where the acetate is reduced to ethanol and esterifies with the 3HPA to form ethyl 3-hydroxypropionate, elevated levels of 3HPA can be recovered in the ester form without loss of activity of the organism. Carboxylic acids, aldehydes and ketones are all capable of esterification. The ester form is biologically inactive as a biocide, but can be used directly in conversion to acrylates or 3-hydroxypropionic acid with the recovery of ethanol.

Example 3

Recovery of 3HPA in the Ester Form by Addition of Ethanol to the Distillate Ethanol can be added to the spent bacterial media to be distilled. This forms the ethyl ester of 3HPA which is more volatile and easier to recover. The 3HPA ester (also referred to as the 3HP ester) can be recovered as an azeotrope in the first 10% of the distillate.

Example 4

The Recovery of 3HP Ester by a Simple Two Step Distillation Process

Step 1:
Spent bacterial media is filtered and 10 liters is distilled in a 10 liter distillation unit with a side arm condenser. The volatile material containing ethyl 3HP is collected in the first 10% of the distillate.

Step 2:
Pooled fractions from Step 1 are re-distilled using fractional distillation. The first 5% is discarded and the ethyl 3HP collected in the next 20% of distillate as a fraction of greater than 90% purity. This fraction typically yields 30% of ethyl 3HP.

Example 5

The Synthesis of Other Esters of 3HP

The addition of ethanol to the growth medium of *Acetobacter lovaniensis* FJ1 has been described under Example 3. Further to this, other esters can be formed by the addition of the corresponding alcohol between C1 and C6 to the growth medium.

Example 6

The Synthesis of Alkaline Earth Salts of 3HPA

The aqueous solution of 3HPA obtained under example 1 can further be converted to either the sodium, potassium or calcium salt by neutralization with sodium hydroxide, potassium hydroxide or calcium hydroxide, respectively in the presence of an oxidising agent such as hydrogen peroxide. The soluble sodium and potassium salts can be recovered by evaporation or freeze drying. The insoluble calcium salt can be recovered by simple filtration.

Example 7

The Synthesis of Ammonium Salts of 3HP

The ammonium salt can be prepared by salt splitting processes such as those described in US 20100099910. The ammonium salts can be further converted to acrylic acid and derivatives using methods well known to those skilled in the art.

Example 8

The Conversion of 3HP to Acrylic Acid

3HP can be converted to acrylic acid by conversion to the ammonium salt followed by treatment with a solid oxide dehydration catalyst (e.g. see U.S. Pat. No. 8,338,145) or other methods such as reactive distillation (e.g. see U.S. Pat. No. 8,198,481). Acrylic acid can further be converted to acrylates, acrylamide and acrylonitrile using standard chemical procedures which are well known to those skilled in the art.

Example 9

The Conversion of Ethyl 3HP to 3HP and Ethanol

The ethyl 3HP can be hydrolysed to the acid product and ethanol in the presence of water and either an acid catalyst or alkaline catalyst. Suitable acid catalysts are sulphuric, phosphoric or hydrochloric acid. Suitable alkaline catalyst are sodium or potassium hydroxide. The ester is reacted with water in the presence of catalyst in a ratio designed to yield 3HP at a given level. During the reaction the ethanol is removed by distillation and the acid product (3HP) recovered.

Example 10

The Conversion of 3HPA to Acrolein

3HPA can be converted to acrolein by acid catalysed oxidative dehydration using standard chemical methods known to those skilled in the art. Acrolein is platform chemical and an alternative route to the synthesis of acrylic acid, acrylates, acrylamide and acrylonitrile.

Example 11

The Recovery of 3HPA

The aldehyde product (3HPA) may be recovered by simple distillation of spent bacterial media followed by concentration either by further distillation or some other suitable method. At concentrations below 10%, 3HPA is present as the monomer or hydrate and at concentrations above 10% as the dimer. The hydrate/monomer form is preferred as generally considered as being safe. After concentration by distillation, the product is passed through a 5-6 micron filter followed by filtration through a 2-3 micron filter to remove debris and cellulose. The pH is adjusted to 7.0 to remove 3-hydroxypropionic acid as the sodium salt which is then recovered by filtration. The filtrate is then further processed to remove residual salts. The filtrate is then filtered through a 0.4 micron filter and stored. The pH of the final 10% solution is typically 7.0-7.5 and shows a UV absorption between 190 and 195 nm typical of the hydrate form, the monomer aldehyde absorbing at longer wavelengths of around 225 nm. This product has been shown to be negative for acrylic acid and acrolein by HPLC. The aldehyde content can be determined by colorimetric assay of Circle et al. (1945) Ind. Eng. Chem. Anal 17 259-262, yielding a yellow colour, whereas acrolein yields a purple colour. This product is further tested for biocidal activity by the ability to kill *Saccharomyces cerevisiae* in a simple challenge test using the Trypan Blue dye exclusion test to determine cell viability after exposure to various dilutions of 3HPA at 37° C. for 24 hours. Dilutions of between 1/10,000 and 1/1,000,000 remain active.

The aldehyde product may also be recovered by partial reduction of the ethyl ester to yield ethanol and 3HPA at higher yield. The direct reduction of the ethyl ester may be effected through the use of DIBAL (H—Al$^i$Bu$_2$). Alternatively, 3HP, after recovery from the ester form, may be converted back directly to 3HPA using a suitable catalyst such as N,N-dimethylchloromethyleneiminium chloride or lithium tri-t-butoxyaluminium hydride (Fuisawa, T., et al. Tetrahedron Letters (1983) 14 1543-1546).

In another application, 3HP recovered from the ester form may be converted to the aldehyde or alcohol derivative using H2 and Pd/C as reductant and catalyst respectively (Falorni, M., et al., *J. Organic Chem.* (1999), 64, 8962-8964).

Example 12

*Acetobacter lovaniensis* does not Produce 1,3 Propanediol from Glycerol

When *Acetobacter lovaniensis* FJ1 is suspended at 10 mg/ml in 250 mM glycerol and fermented anaerobically at 37° C. for 48 hours, analysis by HPLC showed that while 3HPA was synthesised, 1,3 propanediol was absent. A strain of *Lactobacillus* known to produce 3HPA by fermentation, did however co-sysnthesise both 3HPA and 1,3 propanediol. This suggests a different route of synthesis to that shown in *Lactobacillus* and other species which ferment glycerol to 3HPA and 1,3 propanediol. 3HPA produced by fermentation of glycerol by *Acetobacter lovaniensis* FJ1 was shown to be chemically the same as that produced by the *Lactobacillus* strain.

Example 13

3HPA can be Used as a Broad Spectrum Anti-Microbial Agent

The use of 3HPA (Reuterin) as produced from glycerol by *Lactobacillus reuteri* is widely reported. The production and preparation of 3HPA as a commodity chemical broad spectrum anti-microbial agent by *Acetobacter lovaniensis* and *Acetobacter* species is novel, and more commercially useful. The anti-microbial agent is prepared as a 10% aqueous solution of the hydrate 1,1,3 propane triol. The product can be applied under a range of conditions that render it useful as an anti-microbial. Under acidic conditions, the monomer form, cyclic dimer, hemiacetal dimer and the acetal trimer develop. Under alkaline conditions, the aldol dimer, aldol trimer and acetal tetramer develop. The product can be used in a wide variety of applications including but not limited to surface sterilisation in aqueous or alcohol based sprays, gels or powders, sterilisation and preservation of food products such as raw meat, cooked meat, fruit, vegetables and dairy products, as a preservative or anti-microbial agent in cosmetic preparations such as mouth wash, toothpaste, cosmetic creams, cosmetic gels, cosmetic bath preparations, anti-acne preparations, as a preservative or anti-microbial agent in any household or commercial product such as paints, emulsions, adhesives, detergents, and cleaning agents, in industrial processes where an anti-microbial agent is required such as treatment of waste water, waste streams or slurries, agricultural applications such as anti-fungal seed coatings and fertilizer preparations. The 10% aqueous solution of 3HPA is effective at dilutions between 1/1,000 and 1/1,000,000 to target organisms including bacteria, fungi and protozoans.

Example 14

3HPA can be Used as a Primer to Induce Crop Defense Mechanisms

Plants have complex metabolic responses to stress. Stress can take the form of physical attack (herbivores or mechanical cutting), attack by insects and attack by microorganisms including fungi, bacteria and viruses. Plants not only trigger defensive metabolic responses in themselves but also chemically signal plants in the vicinity by the release of an array of chemical signals. One set of compounds are green leaf volatiles derived from linolenic acid are cis 3-hexanal, cis 3-hexanol and cis 3-hexenyl acetate. These compounds in turn oxidise 3HPA and a range of derivatives (J. F. Hamilton et al. (2009) *Atmos. Chem. Phys.*, 9, 3815-3823). These compounds form secondary organic aerosols which trigger defence metabolic pathways in other plants. The application of 3HPA under controlled conditions to green leaf crops would not only impart an anti-microbial activity but also trigger defence metabolism in the target crop. Additional applications would include the cutting of grass where spraying of 3HPA would trigger defensive metabolism and protect the remaining turf, for example on golf courses public parks and recreation areas, reducing the need for watering and application of fertilizers and herbicides.

The invention claimed is:

1. A method for producing 3-hydroxypropanal, the method comprising:
    culturing an *Acetobacter lovaniensis* bacterium in a growth medium containing phosphate at a level which is more than 1 g/liter and nitrate at a level which is more than 0.1 g/liter,
    wherein culturing of the bacterium produces the 3-hydroxypropanal.

2. The method of claim 1, wherein the growth medium contains nitrate at more than 0.6 g/liter.

3. The method of claim 1, wherein the growth medium contains nitrate at more than 1.1 g/liter.

4. The method of claim 1, wherein the growth medium contains nitrate at between 0.6 and 1.8 g/liter.

5. The method of claim 1, wherein the growth medium contains phosphate at more than 10 g/liter.

6. The method of claim 1, wherein the growth medium contains phosphate at more than 13 g/liter.

7. The method of claim 1, wherein the growth medium contains phosphate at between 10 and 30 g/liter.

8. The method of claim 1, wherein the growth medium contains phosphate at between 10 and 30 g/liter and nitrate at between 0.6 and 1.8 g/liter.

9. The method of claim 1, wherein the growth medium does not contain an exogenous source of carbon.

10. The method of claim 1, wherein the growth medium has a pH of between 4 and 7.

11. The method of claim 1, wherein the bacterium is cultured at a temperature of between 15° C. and 30° C.

12. The method of claim 1, wherein the bacterium is cultured until the growth medium reaches an $OD_{600}$ of between 0.75 and 1.00.

13. The method of claim 1, wherein the bacterium is strain FJ1 having accession number NCIMB 41808.

14. The method of claim 1, wherein the method further comprises a step of separating the 3-hydroxypropanal from the growth medium, or separating 3-hydroxypropionic acid or a 3-hydroxypropionate ester from the growth medium where the microorganism has converted some or all of the 3-hydroxypropanal to 3-hydroxypropionic acid and/or a 3-hydroxypropionate ester.

15. The method of claim 1, wherein the method further comprises a step of separating the 3-hydroxypropanal from the growth medium.

16. The method of claim 14, wherein the method further comprises a step of processing the 3-hydroxypropanal, 3-hydroxypropionic acid and/or 3-hydroxypropionate ester into other chemicals such as an ester of 3-hydroxypropionic acid, 3-hydroxypropionic acid, 3-hydroxypropionate salts (including ammonium, sodium and calcium 3-hydroxypropionate), acrylic acid, acrylates, acrylamide, acrylonitrile, acrolein and 1,3 propanediol.

17. The method of claim 1, wherein the method is for producing 3-hydroxypropanal, the method comprising:
- culturing *Acetobacter lovaniensis* strain FJ1 having accession number NCIMB 41808 in a growth medium containing phosphate at a level which is between 10 and 30 g/liter and nitrate at a level which is between 0.6 and 1.8 g/liter; and
- separating the 3-hydroxypropanal from the growth medium.

* * * * *